(12) United States Patent
Besselink et al.

(10) Patent No.: US 8,353,948 B2
(45) Date of Patent: Jan. 15, 2013

(54) FRACTURE-RESISTANT HELICAL STENT INCORPORATING BISTABLE CELLS AND METHODS OF USE

(75) Inventors: Petrus Antonius Besselink, AT Enschede (NL); Mark C. Bates, Charleston, WV (US)

(73) Assignee: CeloNova Stent, Inc., Peachtree City, GA (US)

( * ) Notice: Subject to any disclaimer, the term of this patent is extended or adjusted under 35 U.S.C. 154(b) by 77 days.

(21) Appl. No.: 11/391,940

(22) Filed: Mar. 29, 2006

(65) Prior Publication Data

US 2006/0217795 A1 Sep. 28, 2006

Related U.S. Application Data

(63) Continuation-in-part of application No. 10/270,771, filed on Oct. 11, 2002, which is a continuation of application No. 09/012,843, filed on Jan. 23, 1998, now Pat. No. 6,488,702.

(60) Provisional application No. 60/036,359, filed on Jan. 24, 1997.

(51) Int. Cl.
*A61F 2/06* (2006.01)

(52) U.S. Cl. .................................................. 623/1.15

(58) Field of Classification Search ............... 623/1.15, 623/1.11, 1.16, 1.38, 1.46, 1.22, 1.18, 1.2, 623/1.34, 1.42

See application file for complete search history.

(56) References Cited

U.S. PATENT DOCUMENTS

| | | | |
|---|---|---|---|
| 3,069,125 A | 12/1962 | Hewitt, Jr. | |
| 3,508,587 A | 4/1970 | Mauch | |
| 3,657,744 A | 4/1972 | Ersek | |
| 3,898,717 A | 8/1975 | Schwartz | |
| 4,580,568 A | 4/1986 | Gianturco | |
| 4,655,771 A | 4/1987 | Wallsten | |
| 4,665,906 A | 5/1987 | Jervis | |
| 4,665,918 A | 5/1987 | Garza et al. | |
| 4,733,665 A | 3/1988 | Palmaz | |
| 4,739,762 A | 4/1988 | Palmaz | |
| 4,740,207 A | 4/1988 | Kreamer | |
| 4,886,062 A | 12/1989 | Wiktor | |
| 4,950,258 A | 8/1990 | Kawai et al. | |
| 4,969,890 A | 11/1990 | Sugita et al. | |
| 4,990,155 A | 2/1991 | Wilkoff | |
| 4,994,071 A | 2/1991 | MacGregor | |

(Continued)

FOREIGN PATENT DOCUMENTS

DE 8812719 11/1989

(Continued)

OTHER PUBLICATIONS

U.S. Appl. No. 10/782,266 and its prosecution history including the Final Office Action mailed on Jul. 18, 2008 and Amendment filed on Oct. 20, 2008, filed Feb. 18, 2004, Besselink.

(Continued)

*Primary Examiner* — S. Thomas Hughes
*Assistant Examiner* — Jocelin Tanner
(74) *Attorney, Agent, or Firm* — Rissman Hendricks & Oliverio LLP (57) ABSTRACT

Vascular prostheses and methods of use are provided, wherein the vascular prosthesis includes a plurality of bistable unit cells configured to form a helical structure. A visualization catheter also is provided for use ensuring accurate measurement of a lesion and ensuring delivery and placement of the vascular prosthesis.

51 Claims, 6 Drawing Sheets

U.S. PATENT DOCUMENTS

| | | | |
|---|---|---|---|
| 5,102,417 A * | 4/1992 | Palmaz | 606/195 |
| 5,104,404 A | 4/1992 | Wolff | |
| 5,141,360 A | 8/1992 | Zeman | |
| 5,147,370 A | 9/1992 | McNamara et al. | |
| 5,192,307 A | 3/1993 | Wall | |
| 5,195,984 A | 3/1993 | Schatz | |
| 5,197,978 A | 3/1993 | Hess | |
| 5,226,913 A * | 7/1993 | Pinchuk | 140/71 R |
| 5,234,448 A | 8/1993 | Wholey et al. | |
| 5,282,823 A * | 2/1994 | Schwartz et al. | 623/1.22 |
| 5,383,892 A | 1/1995 | Cardon et al. | |
| 5,383,926 A | 1/1995 | Lock et al. | |
| 5,397,355 A | 3/1995 | Marin et al. | |
| 5,403,341 A | 4/1995 | Solar | |
| 5,411,507 A | 5/1995 | Heckele | |
| 5,449,373 A | 9/1995 | Pinchasik et al. | |
| 5,496,365 A | 3/1996 | Sgro | |
| 5,500,013 A | 3/1996 | Buscemi et al. | |
| 5,545,208 A * | 8/1996 | Wolff et al. | 623/1.22 |
| 5,545,210 A * | 8/1996 | Hess et al. | 128/898 |
| 5,554,183 A | 9/1996 | Nazari | |
| 5,556,413 A | 9/1996 | Lam | |
| 5,562,690 A | 10/1996 | Green et al. | |
| 5,601,593 A * | 2/1997 | Freitag | 623/1.19 |
| 5,628,787 A | 5/1997 | Mayer | |
| 5,643,314 A | 7/1997 | Carpenter et al. | |
| 5,695,516 A | 12/1997 | Fischell et al. | |
| 5,697,971 A * | 12/1997 | Fischell et al. | 623/1.15 |
| 5,702,419 A | 12/1997 | Berry et al. | |
| 5,725,572 A * | 3/1998 | Lam et al. | 623/1.16 |
| 5,733,303 A | 3/1998 | Israel et al. | |
| 5,755,774 A | 5/1998 | Pinchuk | |
| 5,755,776 A | 5/1998 | Al-Saadon | |
| 5,776,181 A | 7/1998 | Lee et al. | |
| 5,776,183 A * | 7/1998 | Kanesaka et al. | 623/1.15 |
| 5,807,404 A * | 9/1998 | Richter | 623/1.16 |
| 5,824,040 A * | 10/1998 | Cox et al. | 623/1.35 |
| 5,861,025 A | 1/1999 | Boudghene et al. | |
| 5,871,538 A * | 2/1999 | Dereume | 128/898 |
| 5,876,449 A | 3/1999 | Starck et al. | |
| 5,891,191 A | 4/1999 | Stinson | |
| 5,895,406 A * | 4/1999 | Gray et al. | 623/1.15 |
| 5,899,882 A * | 5/1999 | Waksman et al. | 604/103.07 |
| 5,913,897 A * | 6/1999 | Corso et al. | 623/1.15 |
| 5,922,020 A * | 7/1999 | Klein et al. | 623/1.15 |
| 5,928,280 A | 7/1999 | Hansen et al. | |
| 6,013,854 A | 1/2000 | Moriuchi | |
| 6,019,789 A | 2/2000 | Dinh et al. | |
| 6,027,526 A * | 2/2000 | Limon et al. | 623/1.15 |
| 6,027,527 A | 2/2000 | Asano et al. | |
| 6,042,606 A | 3/2000 | Frantzen | |
| 6,063,113 A | 5/2000 | Kavteladze et al. | |
| 6,106,548 A | 8/2000 | Roubin et al. | |
| 6,193,744 B1 | 2/2001 | Ehr et al. | |
| 6,203,569 B1 * | 3/2001 | Wijay | 623/1.15 |
| 6,206,911 B1 | 3/2001 | Milo | |
| 6,261,319 B1 | 7/2001 | Kveen et al. | |
| 6,264,685 B1 | 7/2001 | Ahari | |
| 6,368,355 B1 | 4/2002 | Uflacker | |
| 6,451,052 B1 | 9/2002 | Burmeister et al. | |
| 6,464,720 B2 | 10/2002 | Boatman et al. | |
| 6,485,524 B2 | 11/2002 | Strecker | |
| 6,488,702 B1 | 12/2002 | Besselink | |
| 6,540,777 B2 | 4/2003 | Stenzel | |
| 6,582,461 B1 | 6/2003 | Burmeister et al. | |
| 6,669,718 B2 | 12/2003 | Besselink | |
| 6,755,856 B2 | 6/2004 | Fierens et al. | |
| 6,772,836 B2 | 8/2004 | Schetky et al. | |
| 6,799,637 B2 | 10/2004 | Schetky et al. | |
| 7,235,097 B2 | 6/2007 | Calisse et al. | |
| 7,291,166 B2 | 11/2007 | Cheng et al. | |
| 7,300,458 B2 | 11/2007 | Henkes et al. | |
| 7,476,245 B2 | 1/2009 | Abbate | |
| 2001/0027339 A1 | 10/2001 | Boatman et al. | |
| 2001/0044652 A1 * | 11/2001 | Moore | 623/1.16 |
| 2003/0074052 A1 | 4/2003 | Besselink | |
| 2003/0199969 A1 | 10/2003 | Steinke et al. | |
| 2004/0034402 A1 | 2/2004 | Bales et al. | |
| 2004/0088043 A1 | 5/2004 | Klein | |
| 2004/0133270 A1 | 7/2004 | Grandt | |
| 2004/0193247 A1 | 9/2004 | Besselink | |
| 2005/0055080 A1 | 3/2005 | Istephanous et al. | |
| 2005/0163821 A1 | 7/2005 | Sung et al. | |
| 2005/0182479 A1 | 8/2005 | Bonsignore et al. | |
| 2006/0241739 A1 | 10/2006 | Besselink et al. | |
| 2008/0097571 A1 | 4/2008 | Denison et al. | |

FOREIGN PATENT DOCUMENTS

| | | |
|---|---|---|
| EP | 0 274 846 A1 | 7/1988 |
| EP | 0 326 426 A2 | 8/1989 |
| EP | 0 335 341 A1 | 10/1989 |
| EP | 0 364 787 A1 | 4/1990 |
| EP | 0364787 | 4/1990 |
| EP | 0 421 729 A2 | 4/1991 |
| EP | 0421729 | 4/1991 |
| EP | 0 540 290 A2 | 5/1993 |
| EP | 0587 197 A1 | 3/1994 |
| EP | 0587197 | 3/1994 |
| EP | 0 636 345 A1 | 2/1995 |
| EP | 0636345 | 2/1995 |
| EP | 0 664 107 A1 | 7/1995 |
| EP | 0 679 372 A2 | 11/1995 |
| EP | 0679372 | 11/1995 |
| EP | 0 688 545 A1 | 12/1995 |
| EP | 0 734 698 A2 | 10/1996 |
| EP | 0 744 164 A1 | 11/1996 |
| EP | 0744164 | 11/1996 |
| FR | 2 617 721 A1 | 1/1989 |
| FR | 2 642 812 A1 | 8/1990 |
| FR | 2642812 | 8/1990 |
| GB | 2 081 173 A | 2/1982 |
| GB | 2081173 | 2/1982 |
| GB | 2 169 515 A | 7/1986 |
| GB | 2169515 | 7/1986 |
| GB | 2 175 824 A | 12/1986 |
| WO | WO 92/06734 A1 | 4/1992 |
| WO | WO 92/19310 A1 | 11/1992 |
| WO | WO 93/22986 A1 | 11/1993 |
| WO | WO9322986 | 11/1993 |
| WO | WO 94/03127 A1 | 2/1994 |
| WO | WO 95/09584 A1 | 4/1995 |
| WO | WO 95/31945 A1 | 11/1995 |
| WO | WO 95/32757 A1 | 12/1995 |
| WO | WO9532757 | 12/1995 |
| WO | WO 96/03942 A2 | 2/1996 |
| WO | WO9603942 | 2/1996 |
| WO | WO 96/09013 A1 | 3/1996 |
| WO | WO 96/18359 A2 | 6/1996 |
| WO | WO9618359 | 6/1996 |
| WO | WO 96/29028 A1 | 9/1996 |
| WO | WO9629028 | 9/1996 |
| WO | WO 96/41589 A1 | 12/1996 |
| WO | WO 97/04721 A1 | 2/1997 |

OTHER PUBLICATIONS

U.S. Appl. No. 11/317,495 and its prosecution history including the Office Action mailed on Oct. 30, 2008, filed Dec. 22, 2005, Besselink et al.

* cited by examiner

FRACTURE-RESISTANT HELICAL STENT INCORPORATING BISTABLE CELLS AND METHODS OF USE

REFERENCE TO RELATED APPLICATIONS

The present application is a continuation-in-part of U.S. patent application Ser. No. 10/270,771, filed Oct. 11, 2002, which is a continuation of U.S. patent application Ser. No. 09/012,843, filed Jan. 23, 1998, now U.S. Pat. No. 6,488,702, which claims the benefit of priority of U.S. provisional application Ser. No. 60/036,359, filed Jan. 24, 1997.

FIELD OF THE INVENTION

The present invention relates to vascular prostheses, and in particular to vascular prostheses for use in vessels that are subject to cyclic axial or torsional loading, such as may occur in the superficial femoral arteries. In particular, the present invention relates to vascular prostheses comprising a plurality of helically arranged bistable cells.

BACKGROUND OF THE INVENTION

Vascular prostheses, commonly referred to as "stents," are now widely used in interventional procedures for treating lesions of the coronary arteries and other vessels. Such devices generally have a tubular shape and are deployed in a vessel to restore and maintain the patency of a segment of a vessel. More recently, such vascular prostheses have been used in combination with local drug delivery and/or radiation therapy to prevent restenosis of a vessel.

Previously-known vascular prostheses are generally either self-expanding or plastically deformable, and such stents have been used outside the cardiac vasculature with mixed success. Whereas stenting is most commonly performed to treat narrowing of the cardiac vessels, more recent efforts have focused on the use of such devices to treat occlusive diseases of the carotid arteries, renal arteries and superficial femoral arteries. Stents used for such applications frequently require a different set of structural characteristics than those typically used in cardiac stenting.

U.S. Pat. No. 4,733,665 to Palmaz is typical of plastically deformable stents, which are delivered transvascularly via a balloon catheter. The stents described in that patent consist of a wire mesh tube or slotted metal tube. The stents are crimped around the balloon of a delivery catheter, and deployed by inflating the balloon at high pressure to plastically deform and expand the struts of the stent. Although such stents have proved adequate for treating occlusive disease of the cardiac vessels, they are subject to a number of well-documented drawbacks when used outside the cardiac vasculature.

For example, previously known plastically deformable stents generally are not appropriate for blood vessels that are subject to compressive or other forms of dynamic loading, such as the arteries in the extremities or the carotid arteries. While they generally provide adequate radial strength, they typically also have a high degree of axial rigidity. Thus, plastically deformable stents should not be employed in vessels that routinely experience longitudinal shape changes, because the stents lack flexibility to conform to the vessel, and may fracture, deform or cause dissection of the vessel.

Much effort has been expended in the last decade on designing flexible axial links that permit adjacent circumferential rings of a plastically deformable stent to bend and conform to the shape of a vessel during delivery, e.g., as described in U.S. Pat. No. 5,195,984 to Schatz. Such links, however, also comprise a plastically deformable material. Although the links are capable of undergoing a limited amount of bending strain during initial deployment, they will quickly work-harden and fracture when subjected to multiple bending cycles, e.g., in a peripheral vessel that is subject to bending.

Additionally, because plastically deformable stents have very little resilience, the stents of the foregoing patents are not suitable for use in vessels that are subject to high radially compressive forces, such as the carotid arteries. Because the carotid arteries lie relatively close to the surface of the neck, there is a substantial risk that the stent may be inadvertently crushed by a blow or other pressure to the neck. For this reason, self-expanding stents, such as the mesh-tube structures described in U.S. Pat. No. 4,655,771 to Wallsten, and tubes formed of superelastic shape memory materials have been the primary focus for vessels subject to dynamic loading.

Self-expanding stents generally are formed as wire mesh tubes, such as in the above-described patent to Wallsten, tubes comprising single or multiple circumferential rings, such as described in U.S. Pat. No. 4,580,568 to Gianturco, coiled sheets, as described in U.S. Pat. No. 4,740,207 to Kreamer, or self-expanding helixes, as described in U.S. Pat. No. 4,665,918 to Garza et al.

Self-expanding wire mesh tubes of the type described in the above patent to Wallsten, and coiled sheet tubes as described in the above patent to Kreamer, provide a high degree of crush resistance, but only limited capability to flex longitudinally or sustain axial compressive loads. Self-expanding ring structures, such as described in the above patent to Gianturco, also provide good crush radial crush resistance, but do not provide high radial strength, and are subject to migration if subjected to cyclic compression.

Perhaps most promising for such applications, helical stents of the type described in the foregoing patent to Garza appear capable of withstanding longitudinal flexure and radial compressive loads. However, even self-expanding helical stents are not expected to perform adequately when subjected to cyclic axially compressive and/or torsional loading, such as encountered in the superficial femoral arteries ("SFA").

The femoral arteries extend from the iliac arteries in the groin region towards the lower extremities, with the SFAs supplying blood to the knees and feet. Patients suffering from diseases that occlude these vessels, such as arteriosclerosis and vascular complications of diabetes, often may suffer reduced mobility and in extreme cases, may require amputation.

During flexure of the thigh, the femoral artery is subjected to axial compression and/or torsion, which are expected to cause a self-expanding helical stent to undergo radial compression. When such compression is accompanied by shortening of the vessel, the stent is likely to migrate away from its delivery site once the compressive load is removed and the vessel radially re-expands. Although the elastic behavior of the stent is desirable and permits the stent to cope with radial compressive loads, this same feature exacerbates the potential for stent migration when radial compression is accompanied by changes in the vessel length. Consequently, previously known self-expanding helical stents are not expected to perform satisfactorily when deployed in the SFAs and other vessels that experience cyclic axial and/or torsional loading.

In addition to plastically deformable and self-expanding structures, a new type of expandable tubular structure based upon the concept of a "bistable cell" is described in commonly assigned U.S. Patent Application Publication No.

US2004/0193247 to Besselink, which is a publication of U.S. application Ser. No. 10/782,266, and which application is incorporated herein by reference in its entirety. As described in that published application, a bistable cell comprises a thick strut joined at its ends to a thin strut so that the thin strut snaps between a stable collapsed and a stable expanded position when subjected to a radially outwardly directed force, but is unstable at any intermediate position.

Although FIG. 10 of the foregoing Besselink application describes the use of flexible links to improve axial flexibility of the stent, as in the above patent to Schatz, that bistable tubular structure would be expected to suffer similar drawbacks to plastically deformable stents when subjected to dynamic axial bending or compressive loads.

In view of the foregoing drawbacks of previously known vascular prostheses, it would be desirable to provide a vascular prosthesis that may be used in blood vessels subject to axial and torsional loading, but which is not prone to migration.

It further would be desirable to provide a vascular prosthesis capable of withstanding high compressive loads without experiencing significant radial strains, thereby avoiding the potential for the axial migration when the compressive loads are accompanied by vessel length changes.

It also would be desirable to provide a vascular prosthesis having high radial strength, but which also is capable of bending along its length with a high degree of resistance to bending fatigue once deployed in a body vessel.

It still further would be desirable to provide a vascular prosthesis having high radial strength, so as to maintain contact with a vessel wall in the presence of compressive loads, but which also is resistant to failure due to cyclically applied axial compressive and tensile loads.

In addition to the lack of a suitable prosthesis design for stenting the SFAs and similar vessels, interventional procedures involving such arteries pose other difficulties, particularly with respect to sizing and placement of stents in those vessels. Generally, it is necessary to ascertain the size, shape, and location of a treatment site, prior to stent placement, to ensure the proper selection of the stent to be used in a particular patient. A number of technologies have been developed to obtain such information, including fluoroscopic visualization using contrast agents, magnetic resonance imaging and computer-assisted tomography. While the latter two methods provide excellent views of the vessel topography, this information typically is static, pre-procedure information, rather than real-time.

In previously known methods for real-time visualization of a target site, a contrast agent is injected into the vessel prior to stent placement to gain information about a treatment site. Often, the use of contrast agents provides less than ideal precision, for example, because the contrast agent tends to disperse once introduced into the bloodstream. This in turn may require the use of larger volumes of contrast agent. In addition, where the vessel is highly occluded, there may be very little flow and thus difficult to assess the size and severity of the occlusion.

Consequently, it would be desirable to provide methods and apparatus for placing a vascular prosthesis within a vessel that reduces the volume of contrast agent required to obtain information about the treatment site.

SUMMARY OF THE INVENTION

In view of the foregoing drawbacks of previously-know vascular prostheses, it is an object of the present invention to provide a vascular prosthesis that may be used in blood vessels subject to axial and torsional loading, and which is not prone to migration.

It also is an object of this invention to provide a vascular prosthesis capable of withstanding high compressive loads without experiencing significant radial strains, thereby avoiding the potential for the axial migration when the compressive loads are accompanied by vessel length changes.

It is a further object of the present invention to provide a vascular prosthesis having high radial strength, and which is capable of bending along its length with a high degree of resistance to bending fatigue once deployed in a body vessel.

It is another object of this invention to provide a vascular prosthesis having high radial strength, so as to maintain contact with a vessel wall in the presence of compressive loads, having high resistance to failure due to cyclically applied axial compressive and tensile loads.

It is a yet further object of the present invention to provide methods and apparatus for placing a vascular prosthesis within a vessel that reduces the volume of contrast agent required to obtain information about the treatment site.

These and other advantages are achieved by providing a vascular prosthesis having a helical body comprising a plurality of interconnected bistable cells. Each bistable cell comprises a thick strut joined at its ends to a thin strut so that the thin strut snaps between a stable collapsed and a stable expanded position when subjected to a radially outwardly directed force, but is unstable at any intermediate position. Adjacent cells are joined to one another to form a helical structure, with the thin and thick struts of the cells generally aligned relative to a longitudinal axis of the helix. Preferably, the prosthesis comprises a shape memory alloy, such as nickel-titanium, and may in addition include a biodegradable polymeric coating for delivering drugs or other bioactive agents.

The vascular prosthesis of the present invention is expected to provide performance superior to that of previously known stent designs. As is common for helical stents, the helical structure of the present invention permits the stent to readily bend relative to the longitudinal axis of the helix, without experiencing high bending stresses. In addition, by providing a gap between adjacent turns of the helix, the stent also will be able to withstand cyclic axial and/or torsional loading.

Further in accordance with the principles of the present invention, a vascular prosthesis comprising a helix of bistable cells is expected to provide superior fracture resistance compared to previously-known helical stent designs. In particular, the vascular prostheses of the present invention are expected to remain firmly engaged with the vessel wall and resist axial migration, even where the axial length of the vessel changes. Because the bistable cells will not undergo large elastic strains when subjected to compressive loads, the individual turns of the helix will be less likely to shift longitudinally with respect to the vessel wall, thereby avoiding migration when the stent is deployed in a vessel subjected to cyclic axial and/or torsional loads.

In accordance with another aspect of the present invention, a visualization catheter is provided that may be used to visualize a vessel in which the stent of the present invention may be implanted. Methods of using the visualization catheter and for implanting the stent also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

The present invention is directed to a vascular prosthesis having a helical configuration and formed of a plurality of bistable cells. The bistable mode of operation of the vascular prosthesis (hereinafter also referred to as a "stent") of the present invention combines the superior fatigue resistance of previously known self-expanding helical stents with the superior resistance to radial compressive forces and positive fixation characteristics of previously known plastically deformable stents. The result is a vascular prosthesis having high radial strength, improved resistance to fatigue fracture and low potential for migration.

The vascular prosthesis of the present invention is expected to be especially advantageous when deployed in blood vessels subject to dynamic loading, such as the superficial femoral artery. Attempts to use self-expanding helical stents and plastically deformable stents in such vessels often resulted in stent failure, due either to fatigue fracture from cyclic axial loading, migration or both.

Figure 1:
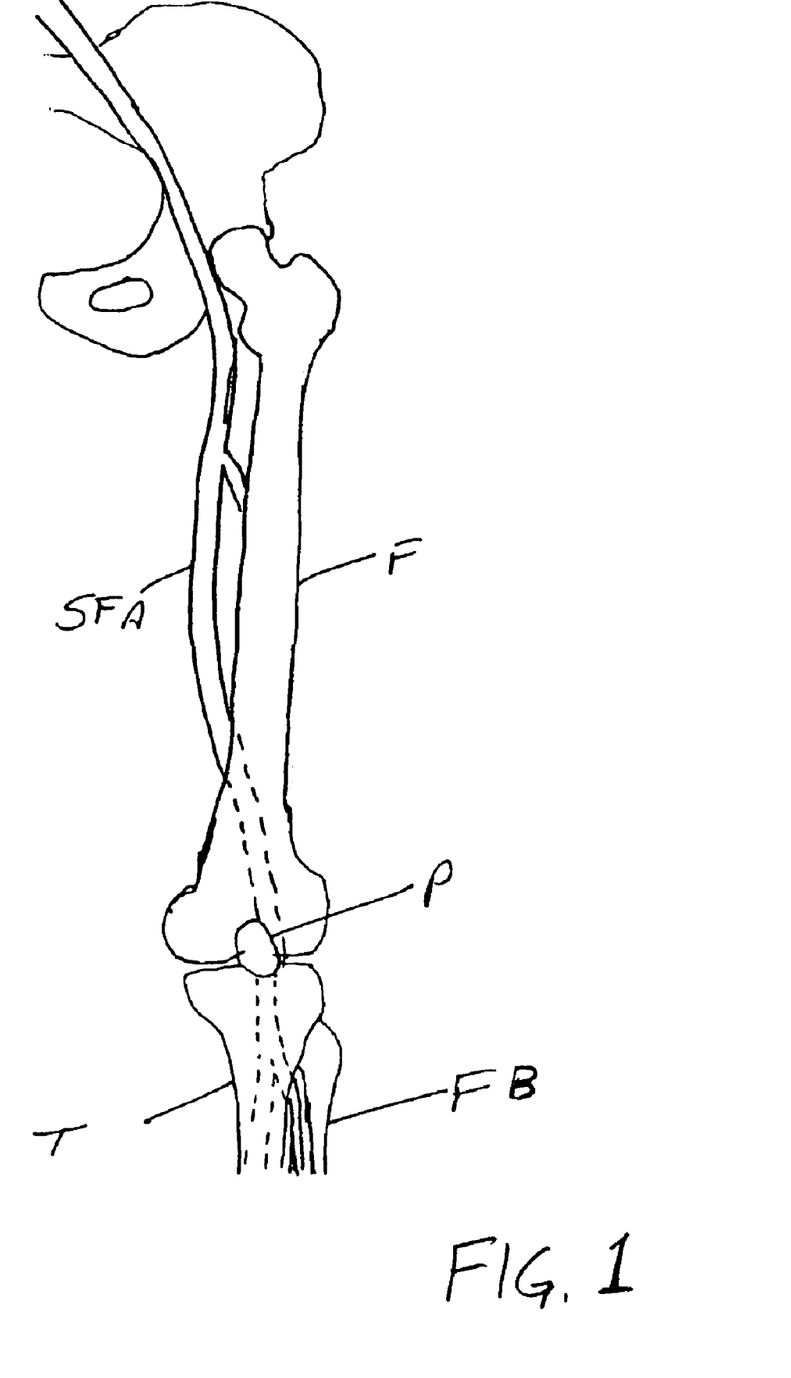
FIG. 1 is a schematic view of the arterial vasculature of a human leg, including the superficial femoral artery ("SFA")

Referring to FIG. 1, an illustrative application for the stent of the present invention is described for treating occlusive disease of the superficial femoral artery, SFA. The location of the SFA in a lower extremity is depicted in relation to femur F, patella P, tibia T, and fibula FB. In particular, SFA passes posteriorly to the bones of the knee. Thus, as the lower extremity undergoes cyclic flexion and extension, the SFA is subjected to varying degrees of tension and compression. It is this cyclic axial loading that is believed to be the cause of failure of previously known stenting attempts in the SFA.

Figures 2A, 2B, 3A, 3B:
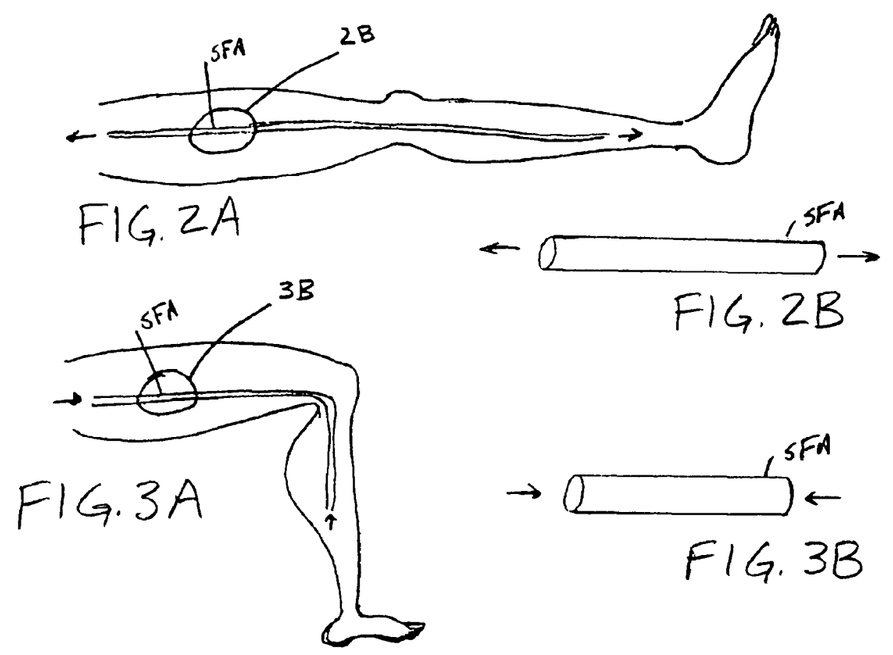
FIGS. 2A and 2B are, respectively, a schematic view of a healthy patient's leg with the knee in the extended position, and a schematic view of the SFA in that position.
FIGS. 3A and 3B are, respectively, a schematic view of a healthy patient's leg with the knee in the bent position, and a schematic view of the SFA in that position.

With respect to FIGS. 2 and 3, loading of the SFA in a healthy patient is now described. In FIG. 2A, a healthy patient's leg is shown with the knee fully extending, such as when the patient is standing. In this position, the SFA is pulled to a straightened, elongated shape and is subjected to tensile forces, as depicted by the arrows in FIG. 2B. In addition to axial loading, such tensile loading also tends to reduce the diameter of the vessel slightly.

By contrast, as depicted in FIG. 3A, when the patient's knee bends, such as when the patient sits or walks, the tensile forces on the SFA are replaced by compressive loads that shorten the length of the vessel. These compressive loads are illustrated by the arrows in FIG. 3B. In addition, the compressive axial loading will tend to cause the diameter of the vessel to expand slightly. In a healthy patient, the SFA remains elastic and responds to cyclical tensile and compressive loading by changing both its length and diameter.

In a patient suffering from arteriosclerosis, a relatively stiff plaque builds up on the interior of the vessel. This stiffening of the arteries may lead to reduced elasticity of the vessel in both the radial and longitudinal directions, thereby substantially reducing the ability of the vessel to cope with cyclical loading. Moreover, because the plaque build-up within the blood vessel typically varies in thickness along the length and circumference of the vessel, the vessel is prone to react non-uniformly to tensile and compressive loads.

Figure 4A:
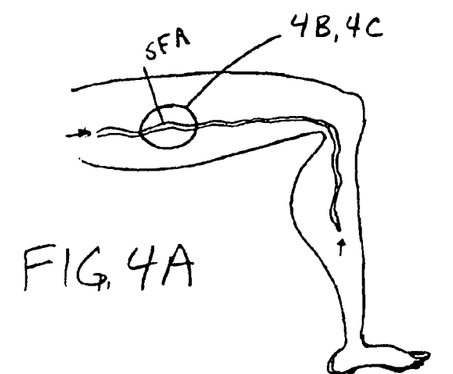
FIGS. 4A, 4B and 4C are, respectively, a schematic view of a patient's leg similar to that of FIG. 3 for a patient suffering from arteriosclerosis, a schematic view of SFA in that position and a schematic view of the SFA when stented with a previously-known stent.
Figure 4B:
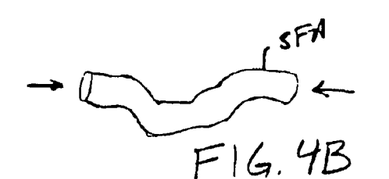

The foregoing phenomenon is illustrated in FIGS. 4A and 4B, which schematically depict how a calcified SFA reacts to the compressive loads applied by flexing of the knee. As the knee bends, the forces applied to the blood vessel transition from tension to compression. Because the plaque deposits prevent radial expansion and uniform shortening of the vessel under compressive loading, the vessel tends to deform and become distorted along its longitudinal axis. As a result, localized regions of the vessel are subjected to concentrated bending and/or compressive loads.

Figure 4C:
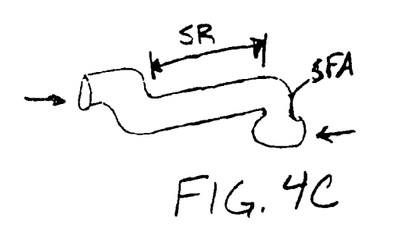

FIG. 4C illustrates the effect of implanting a previously known plastically deformable stent in the vessel of FIGS. 4A and 4B, for example, to relieve ischemia of the lower limbs. As shown in FIG. 4C, the region in which the stent is implanted becomes essentially rigid in both the axial and radial directions. Consequently, when the blood vessel shortens during flexion of the lower extremity, other portions of the SFA compensate for the rigidity of the stented region by incurring greater distortions and deformations. The increased rigidity of the stented region also tends to concentrate vessel bending and distortion near the ends of the stent, thereby increasing the demands on the vessel as well as exacerbating the localized forces applied to the vessel. This may result in the formation of a flow-limiting kink in the vessel.

While use of a previously known self-expanding helical stent to restore patency to an SFA will provide greater axial flexibility, such stents will not provide the sufficient radial strength to avoid stent migration. For example, as a self-expanding helical stent is subjected to repetitive axial loading, localized changes in the diameter of the vessel may cause the diameter of the helical stent to fluctuate. This in turn may cause adjacent turns of the stent helix to shift, with the result that, after many cycles of loading, the stent may migrate from its original deployment site. In densely calcified regions the adjacent cell may tilt and limit flow in the vessel due to concentric focal stress on the stent.

The vascular prosthesis of the present device addresses these problems of previously known stent designs by providing a vascular prosthesis having high longitudinal flexibility, but which provides high radial strength. In particular, the bistable cells of the vascular prosthesis of the present invention provide high radial strength to cope with radial cyclical loads, configured in a helical arrangement that provides axial compressibility and high fracture resistance.

Figures 5A, 5B, 5C, 6, 7A, 7B:
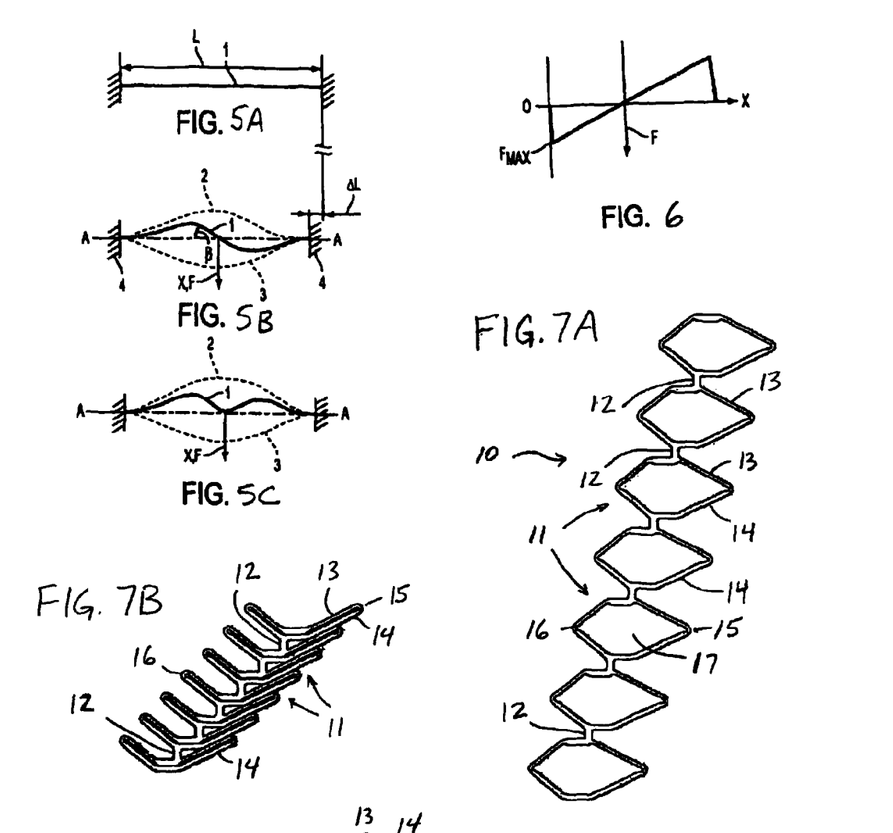
FIGS. 5A-5C illustrate the principle of a bistable mechanism.
FIG. 6 schematically depicts the force-displacement characteristic of the mechanism of FIG. 1.
FIGS. 7A and 7B are, respectively, perspective views of a portion of a vascular prosthesis of the present invention, uncoiled and flattened, in the deployed and delivery configurations.

Referring now to FIGS. 5 and 6, the principle of the bistable mode of operation is described. FIG. 5A depicts rod 1 having length L and fixed at either end. As rod 1 is compressed in the axial direction, it reaches its buckling stress, shown in FIG. 5B, at which the central part of the rod bows outward in a sideways direction, to either position 2 or 3 (shown in dotted lines in FIG. 5B). When the axial displacement ΔL of the ends of rod 1 is held stable by external clamps 4, it is possible to move the central section of the rod between the two stable positions 2 and 3. This movement is in a direction X, perpendicular to the longitudinal axis A-A of the rod. All positions between stable positions 2 and 3 are unstable. As depicted in FIG. 5B, the central part of the rod rotates through angle β before the rod can move in direction X. FIG. 5C shows a second order curvature in rod 1, which occurs when the rotation over angle β is opposed by clamping the central part of rod 1 and maintaining this part parallel to axis A-A.

Referring to FIG. 6, force F required to move the central part of rod 1 through displacement X is plotted as a function of displacement X, with X displayed in the horizontal direction. As rod 1 is moved from upper stable position 2 to lower stable position 3 of FIG. 1, force F increases rapidly from zero to $F_{max}$. At that moment, either the first or second order curvature of FIG. 5B or 5C is reached, and the rod transitions from upper stable position 3 to lower stable position 3. Further displacement in direction X requires less force, because the system has a negative spring rate. The force even becomes zero in the mid position, so that further movement occurs automatically.

It will be observed that the force displacement curve of FIG. 6 is completely symmetrical and thus the force required to move the rod back from the lower to the upper position has the same characteristic. This bistable mode of operation may be accomplished by creating a unit cell in which a thin strut is coupled at its ends to a thick strut, so that the thick strut serves the function of the external clamps 4 of FIGS. 5B and 5C. The thin strut thus will be capable of moving between first and second stable positions via application of an external force, but will be unstable at any intermediate position. The resulting unit cells may be formed into a tubular structure, so that the application of a radially outward force causes the unit cells to expand from a contracted position, in which the thin strut lies adjacent to the thick strut, to an expanded position in which the thin strut is bowed away from the thick strut.

Referring now to FIGS. 7 and 8, a first embodiment of a vascular prosthesis of the present invention is described. Vascular prosthesis 10 is depicted in FIG. 7 unrolled and flattened, e.g., as cut from a sheet of shape memory material, while in FIG. 8, the prosthesis 10 is shown after suitable forming and heat treatment so that the unit cells assume a helical configuration. Prosthesis device 10 comprises plurality of unit cells 11 interconnected by bridges 12. Each unit cell 11 comprises thin strut 13 coupled at its ends to thin strut 14. In accordance with the principles of the present invention, unit cells 11 are bistable.

As described above, unit cells 11 have two stable configurations: an expanded, fully deployed configuration (FIG. 7A) and a collapsed, fully contracted delivery configuration (FIG. 7B). Unit cells 11 resist any force that deform the cells to an intermediate position, until the applied force reaches $F_{max}$, at which the cells transition to the other stable position. The force required to transition thin strut 13 from the delivery configuration to the deployed configuration is a function of the geometry of the cell, the material from which the cell is constructed, and the processing method used to manufacture the prosthesis. Of these, the bistable functionality of the unit cell is strongly influenced by the ratio of the thickness of thin strut 13 to thick strut 14, and thickness ratios of 1:2 to 1:5 are expected to provide good bistable functionality.

Prosthesis 10 may be formed by laser cutting or chemically etching a tube of nickel-titanium alloy or other shape-memory alloy, or alternatively, may be constructed from stainless steel, or other material, such as a biocompatible or biodegradable polymer. Alternatively, prosthesis 10 may be cut or etched from a flat sheet of material, and then formed into a helical tubular member using a mandrel and suitable heat treatments, which are per se known.

Adjacent unit cells 11 are interconnected by bridges 12 offset from one another, so that the unit cells define a helical tubular member. Preferably, the unit cells are dimensioned so that a predetermined number of cells are disposed in a single turn of the helix and form a substantially smooth lumen when deployed in a target vessel. Illustratively, each turn of the helix of prosthesis 10 of FIG. 8 comprises six unit cells, although a greater or lesser number may be used as appropriate for a specific application or vessel.

Still referring to FIGS. 7 and 8, each unit cell 11 comprises distal tip 15 and proximal tip 16, each formed by the junction of the thin and thick struts. Illustratively, the portions of the unit cell that join to form distal tip 15 are longer, and form a more acute angle, than the portions that join to form proximal tip 16. It should be understood, however, that the bistable mode of operation may be achieved with unit cells in which the distal and proximal tips are symmetric or even reversed. In accordance with one aspect of the present invention, the junctions of the thin and thick struts may be configured to permit transition of the thin strut from the delivery configuration to the deployed configuration with either plastic deformation or alternatively elastically, i.e., with little or no plastic deformation.

Each unit cell 11, when transitioned to the deployed configuration, defines aperture 17, bounded by thin strut 13 and thick strut 14. In the fully collapsed delivery configuration, thin strut 13 lies adjacent to thick strut 14, thereby reducing the overall diameter of the prosthesis in the delivery configuration. When arranged as depicted in FIGS. 7 and 8, transitioning unit cells 11 from the delivery configuration to the deployed configuration advantageously provides circumferential expansion, without foreshortening of the prosthesis. Accordingly, the distal and proximal tips of unit cells 11 preferably are aligned with longitudinal axis of the lumen formed by the helix.

Figures 8A, 8B:
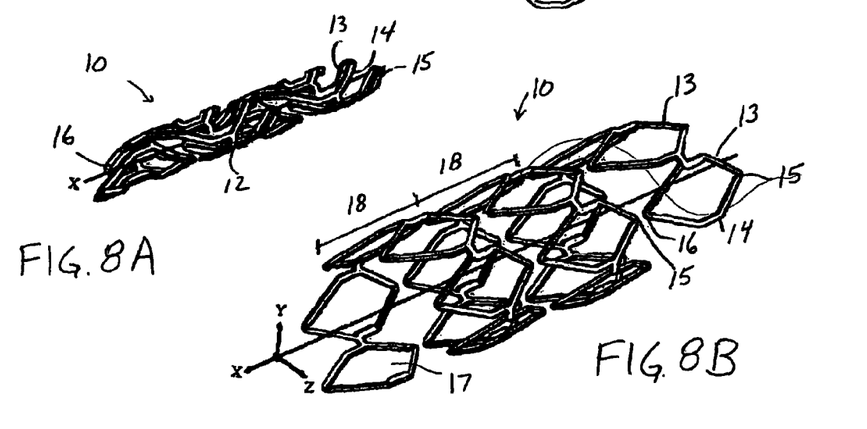
FIGS. 8A and 8B are, respectively, perspective views of a portion of a vascular prosthesis of the present invention in the deployed and delivery configurations.

Referring to FIGS. 8A and 8B, prosthesis 10 of the present invention may comprise any number of unit cells interconnected to form a helix having a plurality of turns. Generally, the length of prosthesis 10 may be selected as appropriate for a specific treatment site or application, and may contain as many unit cells as necessary to provide the desired number of helical turns 18 in the helix. Preferably, distal tips 15 of one turn 18 of the helix are spaced apart a predetermined distance from proximal tips 16 of unit cells 11 of the adjacent turn 18, so that the gap between adjacent turns 18 provides longitudinal flexibility and the ability to withstand compressive loads with the proximal and distal tips of adjacent turns contacting.

This gap may be increased further by arranging the unit cells so that distal tips 15 and proximal tips 16 interdigitate.

Prosthesis 10 may be disposed over a balloon catheter (not shown) inserted along longitudinal axis X, and then crimped down by applying an inwardly directed external force greater than $F_{max}$, so that the unit cells transition to the delivery configuration depicted in FIG. 8A. A suitable delivery catheter for use with prosthesis 10 may comprise any commercially available catheter having a non-compliant or semi-compliant balloon with or without an external protective sheath, as are well-known in the art.

Once the prosthesis and catheter are advanced percutaneously to a desired location within a vessel, the balloon is inflated to apply a radially outwardly directed force to the interior surface of the unit cells. When force applied to the internal surface of the helix of FIG. 8A exceeds $F_{max}$, the thin struts will buckle and transition to the fully expanded deployed configuration of FIG. 8B. Advantageously, because the cells transition to the fully deployed configuration with little or no additional force beyond the transition point, cells 11 will become affixed to the interior surface of the target vessel without the overextension and subsequent recoil experienced with previously-known plastically deformable stents. This in turn is expected to reduce trauma to the vessel lining, and reduce the injury-response mechanism that can lead to neointimal hyperplasia.

In the deployed configuration, distal tip 15 of a cell in one turn 18 of the helix is disposed adjacent to proximal tip 16 of a cell in the adjacent turn 18. It will be appreciated that if there is not a whole number of cells 11 in each turn, distal tips 15 will be offset from proximal tips 16 of adjoining turns 18. For example, if there were six-and-one-half cells 11 per turn 18, distal tips 15 of adjoining turns 18 would be staggered relative to proximal tips 16.

As noted above, the pitch of the helix formed by unit cells 11 may be selected by the design of the cell geometry and placement of bridges 12 to provide a predetermined gap between the distal and proximal tips of adjacent turns. In this manner, prosthesis 10 may be designed for any desired degree of axial flexibility and to accommodate longitudinal displacements between adjacent turns resulting from axially compressive forces.

Referring now to FIG. 9, an alternative embodiment of the prosthesis of the present invention is described, wherein the terminal turns of the prosthesis include additional cells that form annular ends when the prosthesis is deployed within a vessel. In should be understood that in FIG. 9, prosthesis 20 has been unrolled and flattened, whereas in use the prosthesis would be rolled into helical shape.

Prosthesis 20 comprises a series of intermediate turns 21 (similar to prosthesis 10) coupled between proximal and distal terminal turns 22 and 23, respectively. Each of the proximal and distal terminal turns comprises a plurality of unit cells 24 coupled by bridges 25, similar to unit cells 11 and bridges 12 of the embodiment of FIGS. 7 and 8. Unit cells 24 and bridges 25 are configured as described with respect to the embodiment of FIGS. 7 and 8, and operate in a bistable manner as described herein above.

In addition, each of terminal turns 22 and 23 of prosthesis 20 includes additional cells 26, 27, 28 and 29. Proximal terminal turn 22 further includes elongated proximal end 30, while distal terminal turn 23 further includes elongated distal end 31. When deployed within a vessel, additional cells 25-28 and elongated proximal and distal ends 30 and 31, respectively, form annular end regions that provide improved circumferential distribution of forces and thus improved radial strength at the ends of the stent.

Figure 9A:
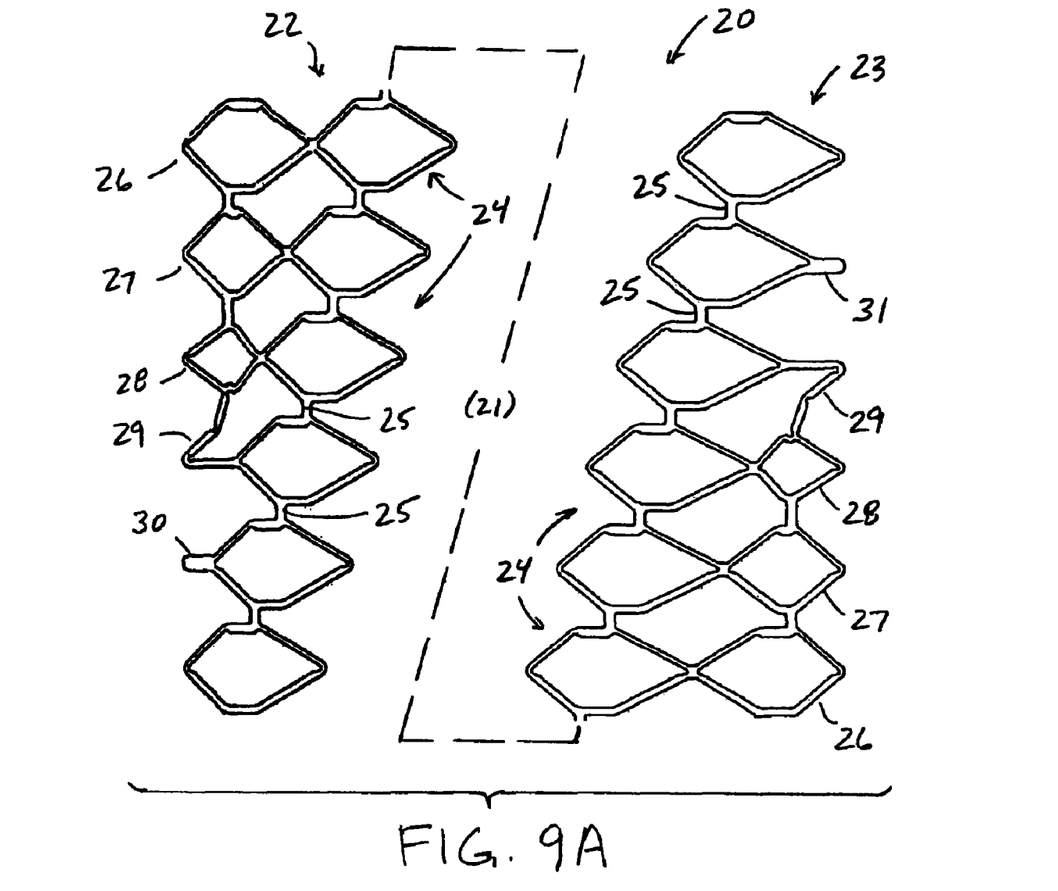
FIGS. 9A and 9B are, respectively, perspective views of an alternative vascular prosthesis of the present invention, uncoiled and flattened, in the deployed and delivery configurations.
Figure 9B:
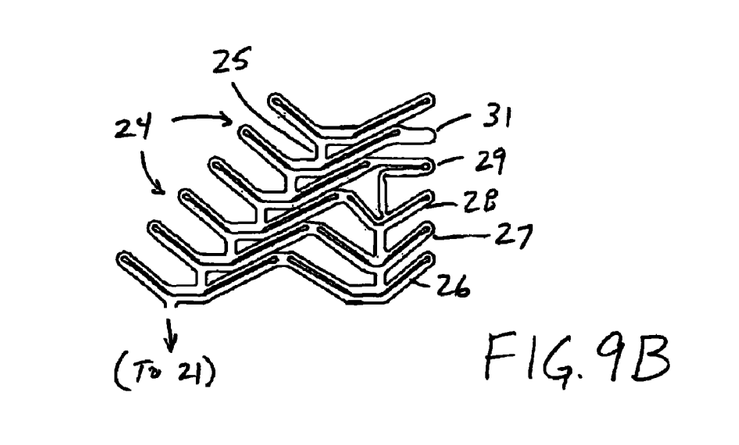

In FIG. 9A, unit cells 24 and additional cells 26-29 are shown in the fully deployed configuration. In FIG. 9B, the unit cells of distal terminal end 23 are shown in the fully collapsed delivery configuration. Elongated proximal end 30 and elongated distal end 31 comprise longitudinal extensions of the respective junction of the thin and thick struts of the corresponding unit cells. Additional cells 25-27 are closed articulating structures configured as bistable cells, while cell 28 is merely an open articulating structure.

Methods of disposing prosthesis 20 on a balloon catheter and implanting the prosthesis at a desired location within a vessel are similar to those described above for the embodiment of FIGS. 7 and 8.

Figures 10A, 10B:
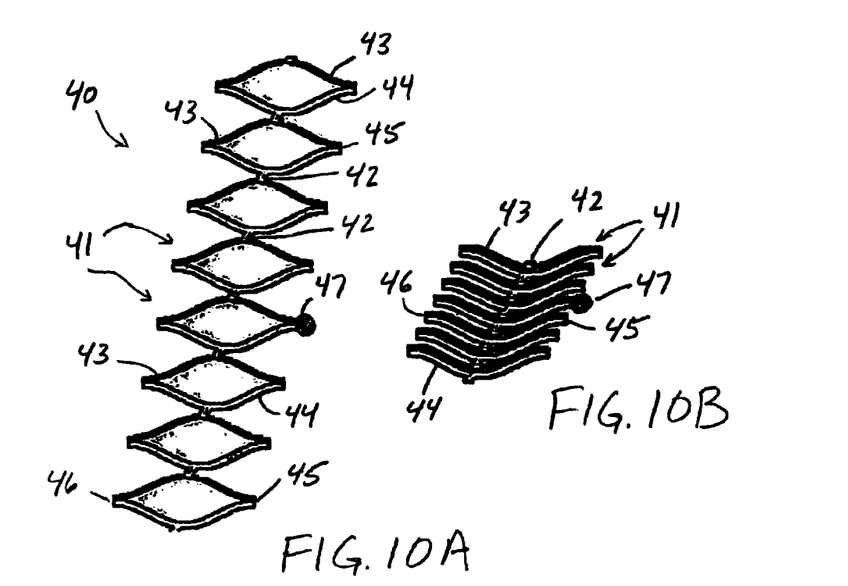
FIGS. 10A and 10B are, respectively, perspective views of a further alternative prosthesis of the present invention, uncoiled and flattened, in deployed and delivery configurations.

Referring now to FIGS. 10A and 10B, a portion of a further alternative embodiment of a vascular prosthesis of the present invention is described. As for the preceding embodiments, prosthesis 40 is shown in FIG. 10 unrolled and flattened, although in use it would be rolled to form a helical structure. Prosthesis 40 comprises plurality of bistable unit cells 41 connected by bridges 42. Each unit cell 41 comprises thin arcuate strut 43 coupled at its ends to thick arcuate strut 44 to form distal and proximal ends 45 and 46, respectively. As depicted in FIG. 10, bridges 42 connect thick strut 44 of one cell to the thin strut of the adjacent cell 43. Alternatively, the adjacent cells could be reversed, so that alternating bridges extend between adjacent pairs of thin or thick struts.

As for the preceding embodiments of FIGS. 7-9, prosthesis 40 forms a series helix having a plurality of adjacent turns. Due to the bistable nature of the unit cells, prosthesis 40 may be compressed onto the balloon of a catheter, and delivered percutaneously to a desired treatment site. Once disposed within a target portion of a vessel or lesion, the balloon may be inflated to transition unit cells 41 from the fully collapsed delivery configuration to the fully expanded deployed configuration.

It will be appreciated that variations in the dimensions of prosthesis 40 may be accomplished by varying the height and width of the unit cells, the length or placement of bridges 42 and/or the pitch of adjacent turns of the helix. In this manner, unit cells 41 of adjacent turns may be caused to interdigitate, so that distal ends 45 of cells 41 in one turn may be positioned between proximal ends 45 of cells 41 in the adjacent turn. Likewise, the distal and proximal turns of the prosthesis 40 may include additional cells or elongated portions, similar to those of the embodiment of FIG. 9, to improve the circumferential force distribution and radial strength of the ends of the prosthesis.

Prosthesis 40 optionally may further include radiopaque markers 47 disposed on distal and/or proximal ends 45 and 46, or elsewhere on the stent, such as on bridges 42. In addition, prosthesis may include a polymeric coating containing drugs or other bioactive agents for delivery into the vessel wall or to prevent restenosis. Alternatively, or in addition, prosthesis 40 may include drug-loaded dimples or pockets formed in thick struts 44 to provide intravascular drug delivery, without affecting the bistable mode of operation of the prosthesis.

In accordance with another aspect of the present invention, a visualization catheter is provided for use in visualizing the target location for implantation of the vascular prostheses described above. With respect to FIG. 11, visualization catheter 50 is configured to assist in placing a guide wire contralaterally across the iliac bifurcation and to provide localized delivery of contrast agent to an intended treatment site.

Figures 11A, 11B:
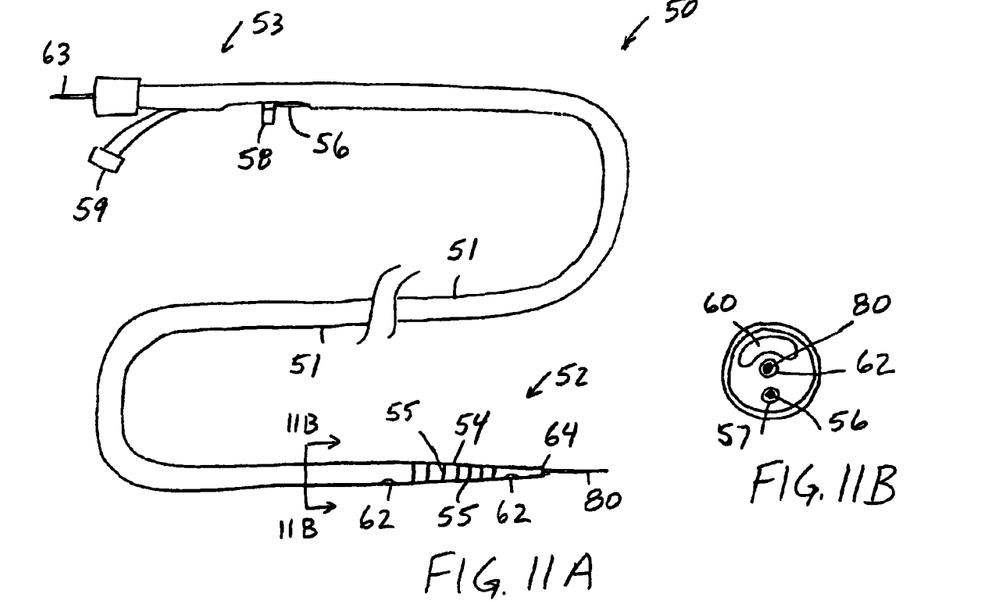
FIGS. 11A and 11B are, respectively, a perspective view and a cross sectional view of a visualization catheter suitable for use with the vascular prosthesis of the present invention.

Visualization catheter 50 comprises flexible elongated body 51 having distal end 52 and proximal end 53. Tapered portion 54 is located near distal end 52, and preferably includes one or more radiopaque markers 55, which may comprise a series of circumferential rings disposed along tapered portion 54. Catheter 50 further includes means for articulating distal end 52, such as pull wire 56 disposed in lumen 57 (FIG. 11B). Pull wire is anchored off-center within distal end 52 and extends proximally through lumen 57 to lever 58. Proximal end 53 also includes contrast injection port 59, which is coupled via lumen 60 to one or more outlet ports 61 disposed in distal end 52.

Lumen 62 extends from the hemostatic port 63 at proximal end 53 to outlet 64 at distal end 52, and is adapted to accommodate a conventional guide wire 80. Lumen 60 provides fluid communication between contrast injection port 59 and outlet ports 61. One or more outlet ports 61 preferably are disposed in the vicinity of tapered portion 54, and more preferably are disposed on either side of radiopaque markers 55. Catheter 50 preferably is constructed of biocompatible materials such as are routinely used in the manufacture of angioplasty and stent delivery catheters.

Lever 58 is configured to permit the clinician to deflect distal end 52 of catheter 50 to route guide wire 80 downward across the iliac bifurcation into the contralateral limb. As discussed in greater detail below, once the catheter is inserted through femoral artery in a patient's leg so that distal end is advanced past the iliac bifurcation, lever 58 may be actuated to direct outlet 64 into the contralateral artery.

In alternative embodiments, visualization catheter may include lighting and/or visualization devices, such as fiber optic cables, CCD or CMOS devices, or other known technology used to visualize the interior of a body vessel.

Next, methods of using the visualization device to assist in implanting the vascular prosthesis of the present invention are described. In one illustrative application of the methods, vascular prosthesis 10 of FIGS. 7 and 8 is implanted within a patient's partially-occluded left superficial femoral artery to restore patency to the vessel and relieve ischemia of the lower limb.

Figure 12A:
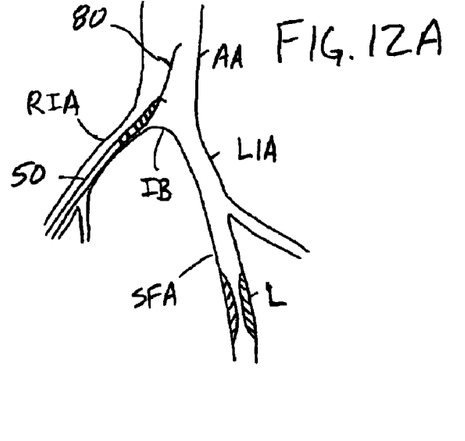
FIGS. 12A-12F illustrate a method of implanting a vascular prosthesis constructed in accordance with the principles of the present invention.

Following routine patient preparation, and the right common femoral artery is accessed via cutdown or Seldinger technique and guide wire 80 is advanced through right iliac artery RIA until it reaches the lower abdominal aorta AA. Visualization catheter 50 then is advanced along guide wire 80 until the distal end passes iliac bifurcation IB, as depicted in FIG. 12A.

Figure 12B:
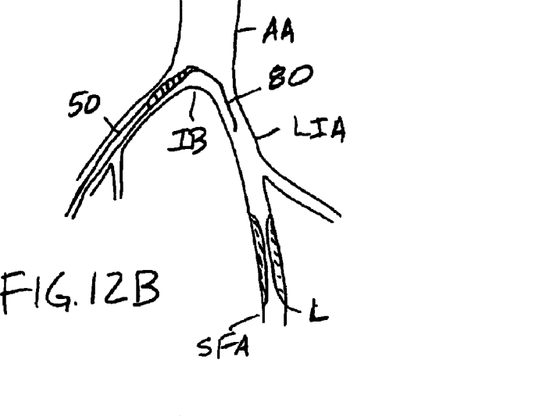

Once distal end 52 is positioned near the iliac bifurcation, e.g., as determined by the location of radiopaque markers using fluoroscopic visualization, guide wire 80 is retracted within distal end 52. Lever 58 then is retracted proximally so that pull wire 56 causes distal end 52 to deflect so that outlet 64 is directed into the left iliac artery, as depicted in FIG. 12B. Guide wire 80 is advanced into the patient's left iliac artery, lever 58 is released, and the visualization catheter is advanced along the guide wire into the left SFA until tapered portion 54 crosses lesion L, as may be determined using fluoroscopic visualization.

Figure 12C:
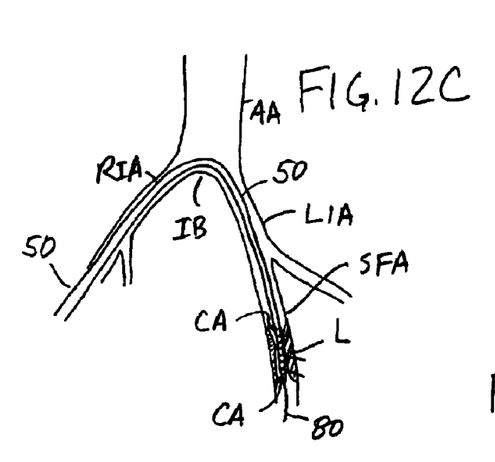

When tapered portion 54 is disposed across the lesion, the clinician injects contrast agent CA through contrast injection port 59 so that the contrast exists through outlet 62 in distal end 52, as depicted in FIG. 12C. In this manner, contrast agent CA may be delivered directly to the treatment site and with minimal dilution, thereby providing better imaging of the lesion topography.

Known visualization techniques then may be employed to measure the location and extent of the lesion, for example, by comparing the size of the lesion to the known dimensions of markings 55. The clinician then uses this information to select an appropriately sized vascular prosthesis and delivery catheter. Once the location and size of the lesion has been established, guide wire 80 may be exchanged for a filter-tipped guide wire 90, and visualization catheter 50 then is withdrawn.

Figure 12D:
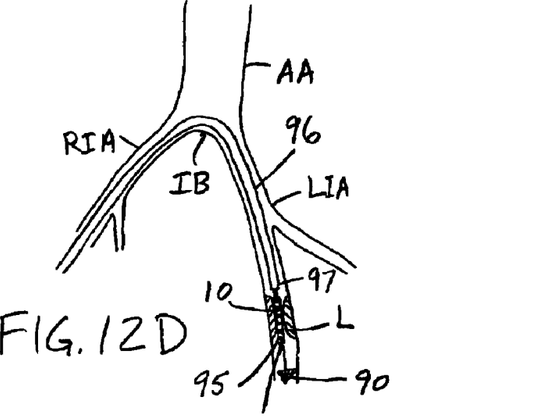

After the clinician has selected an appropriate delivery catheter and prosthesis 10, the delivery catheter and prosthesis are advanced along the filter-tipped guide wire until the stent is disposed across the lesion. In FIG. 12D, prosthesis 10 is disposed in the fully collapsed configuration on balloon 95 of delivery catheter 96. Illustratively, delivery catheter also comprises exterior sheath 97, although the sheath may be omitted. The delivery catheter is then advanced along guide wire 90 until prosthesis 10 is disposed across the lesion, and then sheath 97 is retracted proximally to expose stent 10, as depicted in FIG. 12D.

Figure 12E:
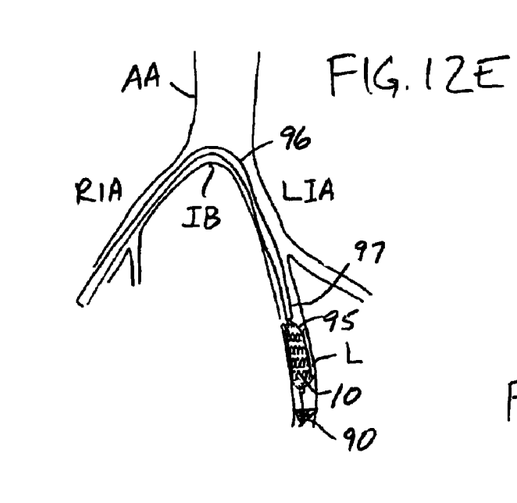

Balloon 95 then is inflated to transition prosthesis 10 to the fully expanded deployed configuration, as shown in FIG. 12E. As the balloon inflates, it applies a radially directed outward force to the interior surface of the prosthesis until the force in the thin struts of the unit cells reaches $F_{max}$ at which point the cells of prosthesis 10 "snap" to the fully expanded deployed configuration. In this manner, prosthesis 10 engages the wall of the vessel without overexpansion or recoil, thereby avoiding the trauma associated with delivery of previously known plastically deformable stents.

Figure 12F:
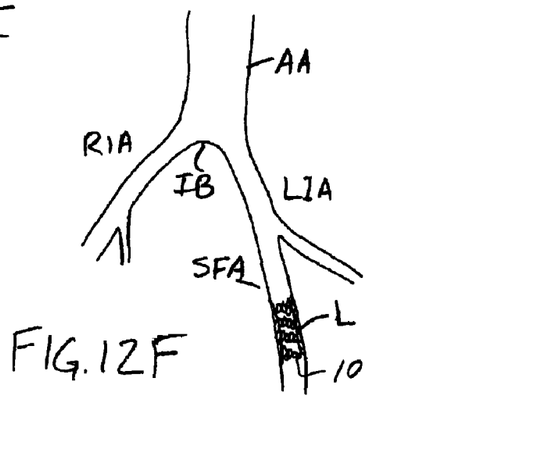

Once prosthesis 10 is deployed, balloon 95 is deflated and conventional imaging techniques may be employed to verify placement of the prosthesis, for example, using radiopaque markers 47 incorporated into the prosthesis. Delivery catheter 96 then is removed, and filter-tipped guide wire 90 then also may be withdrawn, leaving prosthesis 10 deployed in the left SFA, as depicted in FIG. 12F.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. A prosthesis comprising a helical body having a plurality of turns, the plurality of turns comprising unit cells interconnected by bridge elements, one or more of the unit cells having a thin strut including first and second ends coupled to a thick strut having a thickness that is greater than a thickness of the thin strut, the thin strut configured to transition between only a stable fully collapsed configuration and a stable fully expanded configuration, wherein:

for each unit cell, the first and second ends of the thin strut are coupled with corresponding first and second sections of the thick strut; and the thin strut is stable in only the fully collapsed configuration or the fully expanded configuration such that there are no stable states between the fully collapsed configuration and the fully expanded configuration;

wherein the unit cells are arranged such that the first ends and sections of the thin and thick struts respectively are distal of the second ends and sections of the thin and thick struts respectively.

2. The prosthesis of claim 1 further comprising at least one terminal turn, the terminal turn including additional unit cells that define an annular structure when the prosthesis is deployed.

3. The prosthesis of claim 2 wherein at least some of the additional unit cells are bistable cells.

4. The prosthesis of claim 1 wherein the thin strut has a first thickness and the thick strut has a second thickness, and a ratio of the first thickness to the second thickness is between 1:2 and 1:5.

5. The prosthesis of claim 1 wherein the thin strut and the thick strut are elongated in a direction parallel to a longitudinal axis of the helical body.

6. The prosthesis of claim 1, wherein the first end of the thin strut is coupled to the thick strut at a distal end of the unit cell and the second end of the thin strut is coupled to the thick strut at a proximal end of the unit cell, the proximal ends of the unit cells of one turn of the helical body being disposed adjacent to the distal ends of the unit cells of an adjacent turn of the helical body when the prosthesis is deployed.

7. The prosthesis of claim 6 wherein a pitch of the helical body is selected so that a gap is formed between the proximal ends of the unit cells of at least one turn of the helical body and the distal ends of the unit cells of the adjacent turn of the helical body when the prosthesis is deployed.

8. The prosthesis of claim 7 wherein the pitch of the helical body is selected so that the proximal ends of the unit cells of one turn of the helical body are circumferentially offset from the distal ends of the unit cells of the adjacent turn of the helical body when the prosthesis is deployed.

9. The prosthesis of claim 6 wherein a pitch of the helical body is selected so that a gap is formed between the proximal ends of the unit cells of at least two turns of the helical body and the distal ends of the unit cells of the adjacent turn of the helical body when the prosthesis is deployed.

10. The prosthesis of claim 1 wherein the thin strut and the thick strut each has an arcuate shape.

11. The prosthesis of claim 1 wherein each bridge element connects a thin strut of one unit cell to a thick strut of an adjacent unit cell.

12. The prosthesis of claim 1 further comprising one or more radiopaque markers affixed to the helical body.

13. The prosthesis of claim 1 wherein the helical body further comprises a bioactive agent or drug coating.

14. The prosthesis of claim 1 wherein the helical body comprises a shape memory material.

15. The prosthesis of claim 1 wherein the helical body comprises a biodegradable material.

16. The prosthesis of claim 1 wherein the thin strut of at least one of the unit cells comprises a plurality of generally rigid interconnected members.

17. The prosthesis of claim 1 wherein the thin strut of at least one of the unit cells comprises one or more hinges.

18. The prosthesis of claim 1 wherein the thin strut of at least one of the unit cells comprises three generally linear portions, the three generally linear portions cumulatively forming a generally arcuate shape.

19. A kit for treating occlusive disease in a body vessel, the kit comprising:
   a prosthesis comprising a helical body extending along a longitudinal axis and having a plurality of turns, the plurality of turns comprising unit cells interconnected by bridge elements, each of the unit cells having a thin strut including first and second ends coupled to a thick strut having a thickness that is greater than a thickness of the thin strut, the thin strut configured to transition between only a stable fully collapsed configuration and a stable fully expanded configuration, wherein:
      for each unit cell, the first and second ends of the thin strut are coupled with corresponding first and second sections of the thick strut, the second section being proximal of the first section; and
      the thin strut is stable in only the fully collapsed configuration or the fully expanded configuration such that there are no stable states between the fully collapsed configuration and the fully expanded configuration; and
   a visualization catheter comprising an elongated body having a proximal end and a distal end and a guide wire lumen extending therethrough, a tapered portion disposed near the distal end and one or more radiopaque markers disposed on the tapered portion.

20. The kit of claim 19 wherein the visualization catheter further comprises an injection port, one or more outlet ports, and a second lumen extending between the injection port and the one or more outlet ports.

21. The kit of claim 20 wherein the one or more outlet ports are disposed near the tapered portion.

22. The kit of claim 19 wherein the distal end of the elongated body is articulable.

23. The kit of claim 19 wherein the thin strut has a first thickness and the thick strut has a second thickness, and a ratio of the first thickness to the second thickness is between 1:2 and 1:5.

24. The kit of claim 23 wherein the thin strut and the thick strut are elongated in a direction parallel to a longitudinal axis of the helical body.

25. The kit of claim 19 wherein the first end of the thin strut is coupled to the thick strut at a distal end of the unit cell and the second end of the thin strut is coupled to the thick strut at a proximal end of the unit cell, the proximal ends of the unit cells of one turn of the helical body being disposed adjacent to the distal ends of the unit cells of an adjacent turn of the helical body when the prosthesis is deployed.

26. The kit of claim 25 wherein a pitch of the helical body is selected so that a gap is formed between the proximal ends of the unit cells of one turn of the helical body and the distal ends of the unit cells of the adjacent turn of the helical body when the prosthesis is deployed.

27. The kit of claim 26 wherein the pitch of the helical body is selected so that the proximal ends of the unit cells of one turn of the helical body are circumferentially offset from the distal ends of the unit cells of the adjacent turn of the helical body when the prosthesis is deployed.

28. The kit of claim 19 wherein the thin strut and the thick strut each has an arcuate shape.

29. The kit of claim 19 wherein the helical body further comprises a bioactive agent or drug coating.

30. The prosthesis of claim 19 wherein the unit cells are interconnected by bridge elements extending in a helical direction.

31. A prosthesis comprising a helical body having a plurality of turns, the plurality of turns comprising unit cells, each of the unit cells comprising a thin portion having first and second ends directly attached to first and second ends of a thick portion having a thickness that is greater than a thickness of the thin portion, the thin portion configured to transition between a stable collapsed configuration wherein at least a portion of the thin portion is generally concave and a stable expanded configuration wherein at least a portion of the thin portion is generally convex, and wherein a distance that extends from the first end to the second end of the thin portion is approximately the same in the stable collapsed configuration and the stable expanded configuration.

32. The prosthesis of claim 31 wherein one or more of the unit cells are bistable cells.

33. The prosthesis of claim 31 further comprising at least one terminal turn, the terminal turn including additional unit cells comprising an annular structure when the prosthesis is deployed.

34. The prosthesis of claim 31 wherein the first end of the thin portion is coupled to the thick portion at a distal end of the unit cell, the proximal ends of the unit cells of one turn of the helical body disposed adjacent to the distal ends of the unit cells of an adjacent turn of the helical body when the prosthesis is deployed.

35. The prosthesis of claim 34 wherein a pitch of the helical body is selected so that a gap is formed between the proximal ends of the unit cells of one turn of the helical body and the distal ends of the unit cells of the adjacent turn of the helical body when the prosthesis is deployed.

36. The prosthesis of claim 35 wherein the pitch of the helical body is selected so that the proximal ends of the unit cells of one turn of the helical body are circumferentially offset from the distal ends of the unit cells of the adjacent turn of the helical body when the prosthesis is deployed.

37. The prosthesis of claim 31 wherein at least a portion of the thin portion is generally arcuate.

38. The prosthesis of claim 31 wherein the thin portion of at least one of the unit cells comprises a plurality of generally rigid interconnected members.

39. The prosthesis of claim 31 wherein the thin strut of at least one of the unit cells comprises one or more hinges.

40. The prosthesis of claim 31 wherein the thin strut of at least one of the unit cells comprises three generally linear portions, the three generally linear portions cumulatively forming a generally arcuate shape.

41. The prosthesis of claim 31 wherein the unit cells are interconnected by bridge elements extending in a helical direction.

42. A prosthesis comprising a helical body having a plurality of turns, the plurality of turns comprising unit cells interconnected by bridge elements, each of the unit cells comprising a thin strut having first and second ends coupled to a thick strut having a thickness that is greater than a thickness of the thin strut,
the thin strut configured to move from a stable collapsed configuration under outwardly directed radial force to a transition point at which no additional force is needed to further move the thin strut to a stable expanded position such that the thin strut transitions between a stable collapsed configuration and at least one stable expanded configuration, and wherein a distance between the first and second ends of the thin strut is approximately the same in the stable collapsed configuration and the stable expanded configuration; and
a continuous helically oriented gap is formed between the proximal ends of the unit cells of at least one turn of the helical body and the distal ends of the unit cells of an adjacent turn of the helical body along at least a substantial portion of the length of the prosthesis when the prosthesis is deployed.

43. The prosthesis of claim 42 wherein one or more of the unit cells are bistable cells.

44. The prosthesis of claim 42 wherein the continuous helically oriented gap is formed between the proximal ends of the unit cells of at least two turns of the helical body and the distal ends of the unit cells of the adjacent turns of the helical body when the prosthesis is deployed.

45. The prosthesis of claim 42 wherein the continuous helically oriented gap extends along the entire length of the helical body.

46. The prosthesis of claim 42 further comprising at least one terminal turn, the terminal turn including additional unit cells that define an annular structure when the prosthesis is deployed.

47. The prosthesis of claim 42 further comprising a first and a second end portion each comprising a terminal turn, wherein each terminal turn includes additional unit cells that define an annular structure when the prosthesis is deployed and wherein the continuous helically oriented gap extends along the portion of the length of the helical body between the end portions.

48. The prosthesis of claim 42 wherein the first end of the thin strut is coupled to the thick strut at a distal end of the unit cell and the second end of the thin strut is coupled to the thick strut at a proximal end of the unit cell, the proximal ends of the unit cells of one turn of the helical body disposed adjacent to the distal ends of the unit cells of an adjacent turn of the helical body when the prosthesis is deployed.

49. The prosthesis of claim 42 wherein the unit cells are interconnected by bridge elements extending in a helical direction.

50. A prosthesis comprising a helical body having a plurality of turns, the plurality of turns comprising unit cells interconnected by bridge elements, each of the unit cells having a generally longitudinal wave-like thin strut including first and second ends coupled to a generally longitudinal wave-like thick strut having a thickness that is greater than a thickness of the thin strut, the thin strut configured to transition between a stable fully collapsed configuration wherein the thin strut and the thick strut are generally in phase and a stable fully expanded configuration wherein the thin strut and the thick strut are generally out of phase, wherein a distance between the first and second ends of the thin strut is approximately the same in the stable fully collapsed configuration and the stable fully expanded configuration, and
wherein the unit cell is configured to permit the thin strut to transition from the stable fully collapsed configuration to the stable fully expanded configuration without requiring the prosthesis to absorb heat.

51. The prosthesis of claim 50 wherein the thin strut of at least one of the unit cells comprises three generally linear portions, the three generally linear portions cumulatively forming a generally wave-like shape.

* * * * *